US012767932B2

(12) United States Patent
Kim et al.

(10) Patent No.: US 12,767,932 B2
(45) Date of Patent: Oct. 20, 2026

(54) METHOD FOR PREPARING ANIMAL TISSUE-DERIVED BIOMATERIAL, ANIMAL TISSUE-DERIVED BIOMATERIAL PREPARED THEREBY, AND 3D PRINTING METHOD USING SAME

(71) Applicant: T&R BIOFAB CO., LTD., Siheung-si (KR)

(72) Inventors: Hyun Jung Kim, Uiwang-si (KR); Changhwan Kim, Siheung-si (KR); Songmi Lee, Incheon (KR); Young Hwan Kim, Osan-si (KR); Eunhye Park, Ansan-si (KR)

(73) Assignee: T&R BIOFAB CO., LTD., Siheung-si (KR)

( * ) Notice: Subject to any disclaimer, the term of this patent is extended or adjusted under 35 U.S.C. 154(b) by 953 days.

(21) Appl. No.: 17/995,390

(22) PCT Filed: Mar. 17, 2021

(86) PCT No.: PCT/KR2021/003273
§ 371 (c)(1),
(2) Date: Oct. 3, 2022

(87) PCT Pub. No.: WO2021/206303
PCT Pub. Date: Oct. 14, 2021

(65) Prior Publication Data

US 2023/0151337 A1 May 18, 2023

(30) Foreign Application Priority Data

Apr. 6, 2020 (KR) ........................ 10-2020-0041769

(51) Int. Cl.

| | |
|---|---|
| ***C12N 5/06*** | (2006.01) |
| ***B33Y 10/00*** | (2015.01) |
| ***B33Y 70/00*** | (2020.01) |
| ***C12N 5/00*** | (2006.01) |
| ***C12N 5/071*** | (2010.01) |

(52) U.S. Cl.
CPC ............ *C12N 5/0697* (2013.01); *B33Y 10/00* (2014.12); *B33Y 70/00* (2014.12); *C12N 5/0068* (2013.01)

(58) Field of Classification Search
None
See application file for complete search history.

(56) References Cited

U.S. PATENT DOCUMENTS

| | | | |
|---|---|---|---|
| 2005/0013872 | A1 | 1/2005 | Freyman |
| 2007/0014773 | A1 | 1/2007 | Matheny et al. |
| 2017/0232144 | A1 | 8/2017 | Kelly et al. |
| 2018/0353648 | A1 | 12/2018 | Jung et al. |

FOREIGN PATENT DOCUMENTS

| | | | |
|---|---|---|---|
| JP | 2017-522009 | A | 8/2017 |
| JP | 2017-537692 | A | 12/2017 |
| KR | 10-1531479 | B1 | 6/2015 |
| KR | 10-1628821 | B1 | 6/2016 |
| KR | 10-2017-0003916 | A | 1/2017 |
| KR | 10-2018-0135597 | A | 12/2018 |
| KR | 10-2020-0003304 | A | 1/2020 |
| KR | 10-2196026 | B1 | 12/2020 |

OTHER PUBLICATIONS

National Institutes of Health, National Institute of Biomedical Imaging and Bioengineering. “Biomaterials Fact Sheet.” Dec. 2019. (Year: 2019).*
Kim et al. Biofabrication 12 (2020) 025003, pp. 1-14 (Year: 2020).*
Decision to Grant a Patent mailed by the Japanese Patent Office on Sep. 26, 2023, which corresponds to Japanese Patent Application No. 2022-560480 and is related to U.S. Appl. No. 17/995,390.
International Search Report issued in PCT/KR2021/003273; mailed Jun. 18, 2021.

* cited by examiner

*Primary Examiner* — Marcia S Noble
(74) *Attorney, Agent, or Firm* — Studebaker Brackett PLLC

(57) ABSTRACT

Proposed is a method for preparing an animal tissue-derived biomaterial, an animal tissue-derived biomaterial prepared thereby, and a 3D printing method using the same, the method including: a decellularization step of removing cells from the tissue; a liquefaction step of liquefying the extracellular matrix of the decellularized tissue using an acid protease; a filtration step of filtering the decellularized extracellular matrix solution obtained through the liquefaction step; and a sterilization step of sterilizing the mixture obtained through the filtration step.

10 Claims, 1 Drawing Sheet

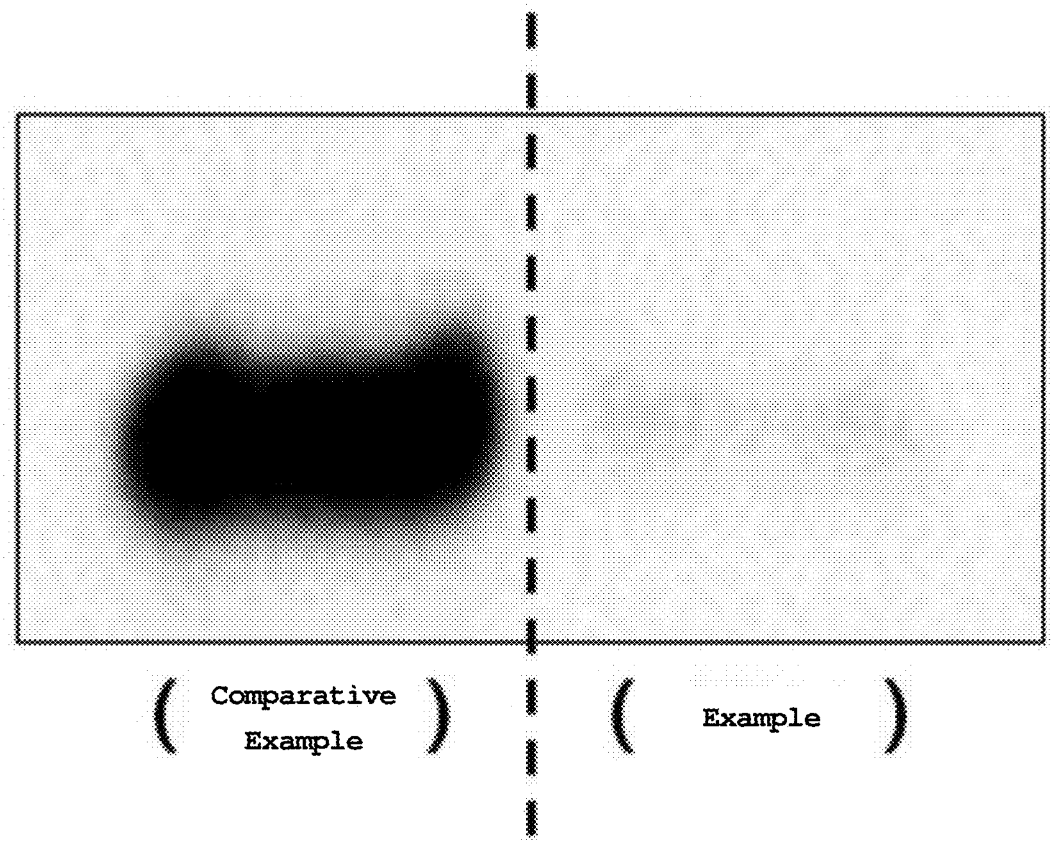
( Comparative Example )
( Example )

METHOD FOR PREPARING ANIMAL TISSUE-DERIVED BIOMATERIAL, ANIMAL TISSUE-DERIVED BIOMATERIAL PREPARED THEREBY, AND 3D PRINTING METHOD USING SAME

CROSS-REFERENCE TO RELATED APPLICATIONS

This application is a U.S. National Phase Entry of International Application No. PCT/KR2021/003273 filed on Mar. 17, 2021, which claims the benefit of priority to Korean Patent Application No. 10-2020-0041769 filed on Apr. 6, 2020, the entire content of which is incorporated herein by reference.

TECHNICAL FIELD

The present disclosure relates to a method for preparing an animal tissue-derived biomaterial, an animal tissue-derived biomaterial prepared thereby, and a three-dimensional printing method using the same. More particularly, the present disclosure relates to an animal tissue-derived biomaterial capable of improving biocompatibility by liquefying a decellularized extracellular matrix and then performing a filtration to remove a component exhibiting cytotoxicity, an animal tissue-derived biomaterial prepared thereby, and a three-dimensional printing method using the same.

BACKGROUND ART

In general, biocompatible materials that are not biotoxic and do not induce an immune response are used when producing artificial tissues for transplantation or research, organs, or organ models for new drug development. In the past, biocompatible polymers such as PLA (poly lactic acid) or PGA (poly glycolic acid) have been used, but recently, biomaterials derived from animal tissues have been in the spotlight.

In particular, studies on biomaterials based on decellularized extracellular matrix (dECM) are being actively conducted. In the case of using such a biomaterial, only the extracellular matrix component from which the cell component has been removed is included, and when used as a bio-ink, the biocompatible polymer provides a more suitable environment for printed cells than a synthetic material-based bio-ink. The biological function of inducing differentiation into a final tissue is significantly superior.

However, biomaterials based on the existing decellularized extracellular matrix contain an acidic protease component used in the process of liquefying the decellularized extracellular matrix and thus exhibit cytotoxicity and can exhibit many side effects during human transplantation and has a problem of lowering storage stability.

Therefore, it is necessary to develop general-purpose biomaterials that can be used as artificial tissues or organs applicable for human transplantation, as well as tissues, organs, or analogs thereof for basic research and animal experimental replacement by reducing biotoxicity and suppressing an immune response.

DISCLOSURE

Technical Problem

The present disclosure provides a method for preparing an animal tissue-derived biomaterial capable of reducing cytotoxicity, suppressing the immune response, and improving storage stability, an animal tissue-derived biomaterial prepared thereby, and a three-dimensional printing method using the same.

Technical Solution

In order to achieve the objective as described above, a method for preparing an animal tissue-derived biomaterial according to an embodiment of the present disclosure includes: decellularizing a tissue to remove cells therefrom; liquefying the extracellular matrix of the decellularized tissue using an acidic protease; filtering the decellularized extracellular matrix solution obtained through the liquefying; and sterilizing the mixture obtained through the filtering.

The filtering may include: separating the decellularized extracellular matrix solution through ultra-filtration into a concentrate and a filtrate; preparing a primary solution through ultra-filtration of the concentrate obtained through the separating; preparing a secondary solution by removing the acidic protease contained in the filtrate obtained through the separating; and mixing the primary solution and the secondary solution.

In addition, the sterilizing may be performed using at least any one of radiation, ethylene oxide, and supercritical carbon dioxide, and drying of the filtered decellularized extracellular matrix solution between the filtering and the sterilizing may be further performed.

The drying may be performed by a freeze-drying method, and a pulverizing in which the decellularized extracellular matrix is pulverized through a wet method between the decellularizing and the liquefying may be further performed.

The pulverizing may be a step of wet pulverization in a solution state after the decellularized extracellular matrix is mixed with an acidic aqueous solution, and in the pulverizing, the pH of the mixture of the decellularized extracellular matrix and the acidic aqueous solution may be in a range of 1 to 4.

The acidic protease used in the liquefying is preferably pepsin, and the liquefying may be performed at a pH range of 1 to 5 and a temperature range of 15° C. to 25° C.

The secondary solution preparing may include: primary treating of removing the acidic protease contained in the filtrate using an ion filter; and secondary treating the treatment solution obtained through the primary treating through ultra-filtration and concentrating.

Another embodiment of the present disclosure may include an animal tissue-derived biomaterial produced by this method.

Another embodiment of the present disclosure includes a three-dimensional printing method using such an animal tissue-derived biomaterial, the method includes: neutralizing the pH of the animal tissue-derived biomaterial; gelling the neutralized solution; and three-dimensional printing to manufacture a three-dimensional structure using the gelled solution.

The neutralizing is a step of adjusting the pH in a range of 6.0 to 8.0, and the gelling may be performed by heating the three-dimensional structure to 30° C. or higher.

A method for preparing an animal tissue-derived biomaterial according to the present disclosure may include: decellularizing a tissue to remove cells therefrom; pulverizing the decellularized extracellular matrix through a wet method; liquefying the extracellular matrix of the decellularized tissue using an acidic protease; filtering the decellularized extracellular matrix solution obtained through the liquefying; drying the filtered decellularized extracellular matrix solution through the freeze-drying method; and sterilizing the mixture obtained through the filtering. The filtering may include: separating the decellularized extracellular matrix solution through ultra-filtration into a concentrate and a filtrate; preparing a primary solution through ultra-filtration of the concentrate obtained through the separating; preparing a secondary solution by removing the acidic protease contained in the filtrate obtained through the separating; and mixing the primary solution and the secondary solution.

Advantageous Effects

According to the present disclosure, the biocompatibility of an animal tissue-derived biomaterial can be improved by liquefying the decellularized extracellular matrix and then performing a filtration to remove components exhibiting cytotoxicity.

In addition, the animal tissue-derived biomaterial, according to the present disclosure, can be stored at room temperature, unlike the existing animal tissue-derived biological material, thereby improving the storage stability of animal tissue-derived biological materials.

DESCRIPTION OF DRAWINGS

FIG. 1 is a photograph showing the results of the experimental example of the present disclosure.

BEST MODE

Hereinafter, before being described in detail through a preferred embodiment of the present disclosure, it will be noted that terms or words used in the present specification and claims should not be limited to general or dictionary meanings but should be interpreted as meanings and concepts conforming to the technical idea of the present disclosure.

Throughout this specification, when a part "includes" a certain component, it means that other components may be further included rather than excluding other components unless otherwise stated.

In addition, "molecular weight" in this disclosure means the weight average molecular weight, and the expression "remove" implies both meanings that specific material is partially or completely removed.

Hereinafter, an embodiment of the present disclosure will be described. However, the scope of the present disclosure is not limited to the following preferred embodiments, and those skilled in the art can implement various modified forms of the contents described herein within the scope of the present disclosure.

The present disclosure relates to a method for preparing an animal tissue-derived biomaterial using a decellularized extracellular matrix, an animal tissue-derived biomaterial prepared thereby, and a three-dimensional printing method using the same.

First, the method for preparing an animal tissue-derived biomaterial according to the present disclosure includes: a decellularization step of removing cells from the tissue; a liquefaction step of liquefying the decellularized extracellular matrix using an acidic protease to prepare a decellularized extracellular matrix solution; a filtration step of filtering the decellularized extracellular matrix solution obtained through the liquefaction step; and a sterilization step of sterilizing the mixture obtained through the filtration step.

In this case, a pulverization step in which the decellularized extracellular matrix is pulverized with a wet method may be further performed between the decellularization step and the liquefaction step.

The decellularization step is a step of obtaining only the decellularized extracellular matrix (dECM) by removing cells from the tissue using a decellularization solution containing a surfactant and a hypertonic solution. The decellularized extracellular matrix may include components such as collagen, elastin, laminin, glycosaminoglycan (GAG), proteoglycans, antibacterial agents, chemoattractants, cytokines, and growth factors.

In the present disclosure, the tissue used to obtain the decellularized extracellular matrix (dECM) is a tissue derived from mammals such as humans, monkeys, pigs, cattle, rabbits, dogs, goats, sheep, chickens, and horses (for example, liver tissue, adipose tissue, bladder tissue, heart tissue, muscle tissue, etc.) may be used, but is not limited thereto.

Surfactants in the decellularization step may include any one or more selected from the group consisting of Triton X-100, Tween 80, sodium dodecyl sulfate (SDS), sodium deoxycholate, and Triton X-200. A hypertonic solution in the decellularization step may be 0.03 to 1.0 M of an aqueous solution containing any one or more salts selected from the group consisting of NaCl, KCl, $CaCl_2$, $MgCl_2$, $BaCl_2$, and $NaHCO_3$ but is not limited thereto.

At this time, using Triton X-100 as a surfactant can effectively destroy DNA contained in cells while minimizing damage to various proteins and glycoproteins and glycosaminoglycan (GAG) contained in the extracellular matrix, so it is desirable to use Triton X-100 as a surfactant.

The decellularized extracellular matrix obtained through the decellularization step may be liquefied after being pulverized through the pulverization step, and since the surface area of the decellularized extracellular matrix is increased through the liquefaction step, the extraction rate of useful components in the liquefaction step using an acidic protease may be improved.

This step is a step in which the decellularized extracellular matrix obtained through the decellularization step is mixed with a high-concentration acidic aqueous solution, and then pulverized in a wet state in a solution state. At this time, the acidic aqueous solution mixed with the decellularized extracellular matrix is a high-concentration acidic aqueous solution, for example, HCl, $CH_3COOH$, $H_3PO_4$, $HNO_3$, $H_2SO_4$, etc., may be used. The pH of the mixture of the acidic aqueous solution and the decellularized extracellular matrix is in a range of 1 to 4. Since the mixture is first exposed to an acidic environment before liquefaction, useful components, particularly collagen, contained in the decellularized extracellular matrix are obtained in the form of acid-soluble collagen, so the yield of collagen can be improved.

On the other hand, in general, when pulverizing tissues, a dry pulverization method in which freeze-drying is followed by pulverization in a solid state is used. During dry pulverizing, there is a problem in that the total working time is increased due to the long time required for the freeze-drying process, and a large amount of powder is lost in the pulverization step after freeze-drying, thereby reducing the yield of useful components. On the other hand, in the present disclosure, the wet sample obtained immediately after the decellularization step is mixed with a high-concentration acidic aqueous solution without performing a separate drying step to perform a pulverizing process in a solution state, thereby significantly reducing the total working time and improving the yield of useful components.

Wet pulverization may be performed using a homogenizer, but other pulverizers can also be used, and the pulverizing speed and time can be variously adjusted according to the amount and type of the objects to be pulverized.

The liquefaction step is a step of preparing a decellularized extracellular matrix solution by liquefying the decellularized extracellular matrix obtained through the decellularization step in order to form an appropriate viscosity when processing an animal tissue-derived biomaterial.

In this step, the decellularized extracellular matrix is decomposed and liquefied by an acidic protease, and since the acid protease has a characteristic that reactivity varies according to pH and temperature conditions, the liquefaction step is preferably performed at a condition of pH range of 1 to 5 and temperature range of 15° C. to 25° C. in order to realize appropriate activity of the acid protease.

In this case, pepsin may be used as the acidic protease, and since the solution containing the decellularized extracellular matrix by adding a high concentration of an acidic aqueous solution in the pulverization step already exhibits strong acidity in the pH range of 1 to 4, it is desirable to adjust the pH of the solution to 1 to 5 by adding a certain amount of water in this step to activate the acidic protease.

The filtering step is a step of filtering the decellularized extracellular matrix solution obtained through the liquefaction step to improve the biocompatibility of animal tissue-derived biological materials by selectively removing cytotoxicity or immune reactions such as acidic proteases or telopeptides while maintaining components such as growth factors that promote tissue regeneration and cytokines.

The filtration step includes: a separation step of ultra-filtering the decellularized extracellular matrix solution into a concentrate and a filtrate; a primary solution preparation step of concentrating the concentrate obtained through the separation step again through ultra-filtration to prepare a primary solution; a secondary solution preparation step of removing the acidic protease contained in the filtrate obtained through the separation step and then concentrating to prepare a secondary solution; and a mixing step of mixing the primary solution and the secondary solution.

First, the separation step is to filter the decellularized extracellular matrix solution with an ultra-filtration membrane of 70 to 100 kDa and separate the filtrate that has passed through the membrane and the concentrate that has not passed through the membrane, and preferably, an ultra-filtration membrane of 70 kDa may be used.

The concentrate obtained in this step contains relatively high molecular weight components such as collagen, elastin, and glycosaminoglycan, and this concentrate is concentrated again through ultra-filtration in the primary solution preparation step 1 and used as a primary solution. In this case, the size of the ultra-filtration membrane used may be 0.1 to 5 kDa, preferably 0.5 to 2 kDa, more preferably 1 kDa.

On the other hand, the filtrate obtained in the separation step contains growth factors, cytokines, acidic proteases, and other low molecular weight decellularized extracellular matrix components.

The acidic protease contained in the filtrate is used to liquefy the decellularized extracellular matrix, but the acidic protease exhibits cytotoxicity and can cause side effects in the human body as an enzyme, and thus artificial organs or tissues manufactured using a biomaterial derived from animal tissues including the acidic protease are difficult to be transplanted to the human body, so there is a problem that their use is limited only for research purposes. In addition, since the animal tissue-derived biomaterial shows activity at the temperature range of 15° C. to 25° C., there was a problem that the animal tissue-derived biomaterial containing acidic protease could not be stored at room temperature.

In the present disclosure, by removing the acidic protease present in the filtrate obtained in the separation step, it is possible to prevent or suppress problems such as cytotoxicity of animal tissue-derived biological materials, induction of immune response, and induction of side effects in the human body, and it is possible to store at room temperature.

Specifically, the secondary solution preparation step includes a primary treatment step of removing the acidic protease contained in the filtrate using an ion filter; and a secondary treatment step of concentrating the treatment solution obtained through the primary treatment step by ultra-filtration; in which the acid protease can be removed in the primary treatment step, and the telopeptide that induces an immune response can be removed in the secondary treatment step.

The primary treatment step is a step of selectively remove only the acidic protease by using the isoelectric point of the acidic protease. Pepsin may be used as the acidic protease, and since the isoelectric point of pepsin is about pH 1, when the pH of a solution containing pepsin is higher than 1, pepsin is negatively charged. Therefore, when the filtrate whose pH is higher than 1 through dilution is passed through the ion filter charged with cations, the acidic protease is adsorbed or ion-exchanged by the ion filter by electrostatic force to be removed, and the remaining components except for the acidic protease are discharged through the ion filter. As such an ion filter, for example, a Sartobind® Q-type filter, can be used.

Since the treatment solution obtained through the primary treatment step still contains telopeptide that induces an immune response, the biocompatibility of the animal tissue-derived biomaterial can be further improved by removing the telopeptide through the secondary treatment step.

The secondary treatment step is a step of concentrating the treatment solution by ultra-filtration and may be a step of obtaining a concentrate after filtering the treatment solution using an ultra-filtration membrane of 1 to 10 kDa, preferably an ultra-filtration membrane of 4 to 6 kDa, more preferably ultra-filtration membrane of 5 kDa.

In the previous liquefaction step, telopeptide is separated from collagen by an acidic protease, and the isolated telopeptide has a low molecular weight of about 0.5 to 4.5 kDa. On the other hand, since useful components such as growth factors and cytokines contained in the treatment solution have a molecular weight of about 5 kDa or more, when the treatment solution is concentrated using an ultra-filtration membrane of the same size in the secondary treatment step, telopeptide is separated into a filtrate together with water, and only growth factors, cytokines, and other low molecular weight decellularized extracellular matrix components separated by an ultra-filtration membrane can be separated into a concentrate.

When the primary solution and the secondary solution are mixed in the subsequent mixing step, an acidic protease such as pepsin and telopeptide is finally removed, so that side effects such as cytotoxicity and immune response induction are removed animal tissue-derived biomaterial can be obtained.

After the filtration step is completed, a sterilization step of sterilizing an animal tissue-derived biomaterial is performed, and as a sterilization method, a sterilization method using at least one of radiation, ethylene oxide, and supercritical carbon dioxide may be used.

As described above, the sterilized animal tissue-derived biomaterial may be used or stored as it is in the phase after sterilization is completed, but if necessary, an additional drying step may be performed and stored in a dried powder state. In this case, a freeze-drying method is preferably used.

Meanwhile, the present disclosure includes an animal tissue-derived biomaterial prepared through the above method and a three-dimensional printing method for producing a three-dimensional structure using the animal tissue-derived biomaterial.

Specifically, the three-dimensional printing method using an animal tissue-derived biomaterial, according to the present disclosure, includes: a neutralization step of neutralizing the pH of the animal tissue-derived biomaterial; a gelation step of gelling the neutralized solution; and a three-dimensional printing step of producing a three-dimensional structure using the gelled solution.

When the previously prepared animal tissue-derived biomaterial exists in a solution state without going through a drying step, the neutralization step is performed immediately during three-dimensional printing, but when the animal tissue-derived biomaterial is powdered through a drying step, a dissolution step of liquefying the powdered animal tissue-derived biomaterial again may be further performed prior to the neutralization step.

The dissolution step may be a step of solubilizing a powdery animal tissue-derived biomaterial with water or an aqueous solution such as saline or buffer solution.

The neutralization step is a step of neutralizing the pH of a liquid animal tissue-derived biomaterial to a neutral region, and in this step, the pH can be adjusted to 6.0 to 8.0, and during neutralization, the animal tissue-derived biomaterial may be mixed with a base or an isotropic buffer and neutralized. In this case, the base that can be used includes, for example, NaOH, KOH, and the like, but is not limited thereto.

Next, a gelation step of gelling the neutralized solution is performed. Since the animal tissue-derived biomaterial obtained through the neutralization step can be gelled at a temperature condition of 30° C. or higher, preferably 37° C. or higher, the solution neutralized in the gelation step is heated to 30° C. or higher for gelation, thereby increasing the viscosity of the animal tissue-derived biomaterial and maintaining a three-dimensional printed shape.

Next, a three-dimensional printing step of producing a three-dimensional structure using the neutralized solution in the neutralization step may be performed.

On the other hand, in the animal tissue-derived biomaterial of the present disclosure, a three-dimensional structure can be formed not only by the above-described three-dimensional printing method but also by administering a neutralized solution obtained through the dissolution step and neutralization step to the patient and then heating to 30° C. or more by another heat source.

As described above, in the present specification, a three-dimensional printing method using an animal tissue-derived biomaterial is presented as an example, but the processing method of an animal tissue-derived biomaterial is not limited thereto. It is obvious to those skilled in the art that the biological material derived from animal tissue of the present disclosure may be processed as it is or in a method other than 3D printing to be applied to various fields such as medical materials, medical devices, and renewable medical products.

Hereinafter, specific actions and effects of the present disclosure will be described through an embodiment of the present disclosure. However, this is presented as a preferred example of the present disclosure, and the scope of the present disclosure is not limited according to the embodiments.

Preparation Example

First, the pig's liver is cut into 1 mm size and prepared into several slices, and then the slices are put in distilled water and washed for 2 hours at room temperature. Decellularization is performed at 10° C. for 8 hours using a decellularized solution containing 0.5% Triton X-100 and 0.5 M NaCl aqueous solution, and the decellularized solution is exchanged with a new solution every 3 hours. Thereafter, the decellularized slices are washed with distilled water, disinfected with a disinfectant solution containing PBS buffer and 0.1% peracetic acid at room temperature for 1 hour, and then washed again with distilled water for 1 hour to prepare decellularized tissue sections.

Next, 40 g of the decellularized tissue sections are mixed with 160 mL of 10 N HCl solution, stirred, and then pulverized 20 times for 1 minute each using a homogenizer. Then, 1,440 ml of water and 0.8 g of pepsin are mixed with the pulverized mixture and stirred at a temperature of 20° C. for 72 hours to liquefy.

Next, the liquefied solution is filtered using a 70 kDa ultra-filtration membrane, and a portion of the filtrate, which is a solution that has passed through the filtration membrane, is used as a sample for Comparative Example. The remaining filtrate was filtered using a Sartobind®Q-type ion filter, and some of the filtrates discharged from the ion filter was used as a sample of the embodiment.

Experimental Example

The expression level of pepsin contained in the samples of Comparative Examples and Examples was investigated using Western blot analysis, and the results are shown in FIG. 1. In this case, ab181878 (Abcam, goat pAb to pepsin), an antibody specifically expressed for pepsin, was used to detect pepsin.

Referring to the experimental results of FIG. 1, the sample of Example showed a significantly more reduced expression of pepsin than the sample of Comparative Example, confirming that the filtration process using an ion filter was effective in removing pepsin.

The present disclosure is not limited to the specific embodiments and descriptions described above, and without departing from the gist of the present disclosure claimed in the claims, anyone with ordinary skill in the art to which the disclosure pertains can make various modifications implementation is possible, and such modifications shall fall within the protection scope of the present disclosure.

INDUSTRIAL APPLICABILITY

An objective of the present disclosure is to provide a method for preparing an animal tissue-derived biomaterial capable of reducing cytotoxicity, suppressing the immune response, and improving storage stability, an animal tissue-derived biomaterial prepared thereby, and a three-dimensional printing method using the same. By liquefying the decellularized extracellular matrix and then performing a filtration step to remove cytotoxic components, the biocompatibility of animal tissue-derived biomaterials can be improved, and since the animal tissue-derived biomaterial can be stored at room temperature, the storage stability of the animal tissue-derived biomaterial can be improved unlike the existing animal tissue-derived biomaterial, and thus industrial applicability exists.

The invention claimed is:

1. A method for preparing an animal tissue-derived biomaterial, the method comprising:

decellularizing a tissue to remove cells from the tissue;

liquefying an extracellular matrix of the decellularized tissue using an acidic protease;

filtering the decellularized extracellular matrix solution obtained through the liquefying; and sterilizing the resulting mixture obtained through the filtering, wherein the filtering comprises:

filtering the decellularized extracellular matrix solution through a 70 to 100 kDa ultra-filtration membrane to obtain a concentrated solution containing collagen, elastin and glycosaminoglycan, and a filtrate containing growth factors, cytokines and the acidic protease;

filtering the concentrated solution through a 0.1 to 5 kDa ultra-filtration membrane to obtain a primary solution;

filtering the filtrate to remove the acidic protease contained in the filtrate to obtain a secondary solution; and mixing the primary solution and the secondary solution.

2. The method of claim 1, wherein the sterilizing is performed using at least one of radiation, ethylene oxide, and supercritical carbon dioxide.

3. The method of claim 1, further comprising drying the filtered decellularized extracellular matrix solution between the filtering the decellularized extracellular matrix solution and the sterilizing.

4. The method of claim 3, wherein the drying is performed by a freeze-drying method.

5. The method of claim 1, further comprising pulverizing the decellularized extracellular matrix in a wet condition between the decellularizing and the liquefying.

6. The method of claim 5, wherein in the pulverizing, the decellularized extracellular matrix is mixed with an acidic aqueous solution and then wet pulverized in a solution state.

7. The method of claim 6, wherein in the pulverizing, the mixture of the decellularized extracellular matrix and the acidic aqueous solution has a pH in a range of 1 to 4.

8. The method of claim 1, wherein the acidic protease used in the liquefying is pepsin.

9. The method of claim 8, wherein the liquefying is performed at a pH range of 1 to 5 and a temperature range of 15° C. to 25° C.

10. The method of claim 1, wherein the filtering the filtrate to obtain the secondary solution comprises:

a primary treatment step of treating the filtrate to remove the acidic protease contained in the filtrate using an ion filter; and a secondary treatment step of ultra-filtrating and concentrating the treated solution obtained through the primary treatment.

* * * * *